(12) United States Patent
Chew et al.

(10) Patent No.: US 7,373,192 B2
(45) Date of Patent: May 13, 2008

(54) OXIMETER RED AND IR ZERO CALIBRATION CONTROL

(75) Inventors: Bradford B. Chew, San Ramon, CA (US); Ethan Petersen, Castro Valley, CA (US); William Shea, Livermore, CA (US)

(73) Assignee: Nellcor Puritan Bennett Inc., Pleasanton, CA (US)

( * ) Notice: Subject to any disclaimer, the term of this patent is extended or adjusted under 35 U.S.C. 154(b) by 650 days.

(21) Appl. No.: 10/788,239

(22) Filed: Feb. 25, 2004

(65) Prior Publication Data

US 2005/0187449 A1 Aug. 25, 2005

(51) Int. Cl.
*A61B 5/1455* (2006.01)

(52) U.S. Cl. ...................... 600/323; 600/310

(58) Field of Classification Search ................ 600/322, 600/323, 310
See application file for complete search history.

(56) References Cited

U.S. PATENT DOCUMENTS

| | | | |
|---|---|---|---|
| 4,802,486 A | 2/1989 | Goodman et al. | |
| 4,848,901 A * | 7/1989 | Hood, Jr. ................... | 356/41 |
| 4,911,167 A | 3/1990 | Corenman et al. | |
| 4,928,692 A | 5/1990 | Goodman et al. | |
| 4,934,372 A | 6/1990 | Corenman et al. | |
| 5,008,595 A | 4/1991 | Kazar | |
| 5,351,685 A | 10/1994 | Potratz | |
| 5,368,026 A | 11/1994 | Swedlow et al. | |
| 5,662,106 A | 9/1997 | Swedlow et al. | |
| 5,713,355 A | 2/1998 | Richardson et al. | |
| 5,746,697 A | 5/1998 | Swedlow et al. | |
| 5,803,910 A | 9/1998 | Potratz | |
| 5,818,985 A | 10/1998 | Merchant et al. | |
| 5,921,921 A | 7/1999 | Potratz et al. | |
| 5,924,979 A | 7/1999 | Swedlow et al. | |
| 5,961,450 A * | 10/1999 | Merchant et al. ........... | 600/322 |
| 5,995,855 A * | 11/1999 | Kiani et al. ................. | 600/310 |
| 6,226,539 B1 | 5/2001 | Potratz | |
| 6,343,223 B1 | 1/2002 | Chin et al. | |
| 6,490,466 B1 * | 12/2002 | Fein et al. ................... | 600/323 |
| 6,665,551 B1 | 12/2003 | Suzuki | |
| 6,701,091 B2 * | 3/2004 | Escobosa et al. ........... | 398/107 |
| 2001/0002206 A1 | 5/2001 | Diab et al. | |
| 2004/0015093 A1 | 1/2004 | Knapp, II et al. | |
| 2004/0030229 A1 | 2/2004 | Norris | |

FOREIGN PATENT DOCUMENTS

| | | |
|---|---|---|
| RU | 2175523 C1 | 11/2001 |
| WO | WO 2004/047631 A2 | 6/2004 |

* cited by examiner

*Primary Examiner*—Eric Winakur
*Assistant Examiner*—Etsub D Berhanu

(57) ABSTRACT

A pulse oximeter with drive lines for driving red and IR LEDs, and a drive circuit for driving those drive lines. A processor controls the drive circuit using a red zero output line and an IR zero output line directly connected between the processor and the drive circuit. This allows a control signal to directly control the turning off of either the red or IR drive transistors to prevent forward current flow through the red and IR LEDs by overriding the ongoing programmable logic state machine control of the drive transistors. The effects of crosstalk and capacitive coupling are reduced as a result.

7 Claims, 3 Drawing Sheets

OXIMETER RED AND IR ZERO CALIBRATION CONTROL

BACKGROUND OF THE INVENTION

The present invention relates to oximeters, and in particular to LED drive circuits in pulse oximeters.

Pulse oximetry is typically used to measure various blood chemistry characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed at various wavelengths is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

The light sources, typically light emitting diodes (LEDs), need to be driven with current to activate them. In order to reduce the effects of leakage and capacitively coupled transients, it is desirable to be able to drive one of the LEDs, without any current going through the other one. Typically, this can be done by controlling the duty cycle with the processor in the pulse oximeter. However, using the duty cycle controls to eliminate current through one of the LEDs has been discovered to still involve an amount of leakage and capacitively coupled transients that is undesirable.

BRIEF SUMMARY OF THE INVENTION

The present invention provides a pulse oximeter with drive lines for driving red and IR LEDs, and a drive circuit for driving those drive lines. A processor controls the drive circuit using a red zero output line and an IR zero output line directly connected between the processor and the drive circuit. This allows a control signal to directly control the turning off of either the red or IR drive transistors which direct forward current flow through the red and IR LEDs.

In one embodiment, the red and IR zero output lines are connected to a programmed logic circuit. The programmed logic circuit, which is controlled by the processor, provides the various timing signals for the transistors of the drive circuit. In one embodiment, the drive circuit includes an H-bridge circuit with red and IR FET drive transistors.

For a further understanding of the nature and advantages of the present invention, reference should be made to the following description taken in conjunction with the accompanying drawings.

DETAILED DESCRIPTION OF THE INVENTION

Oximeter Front End

Figure 1:
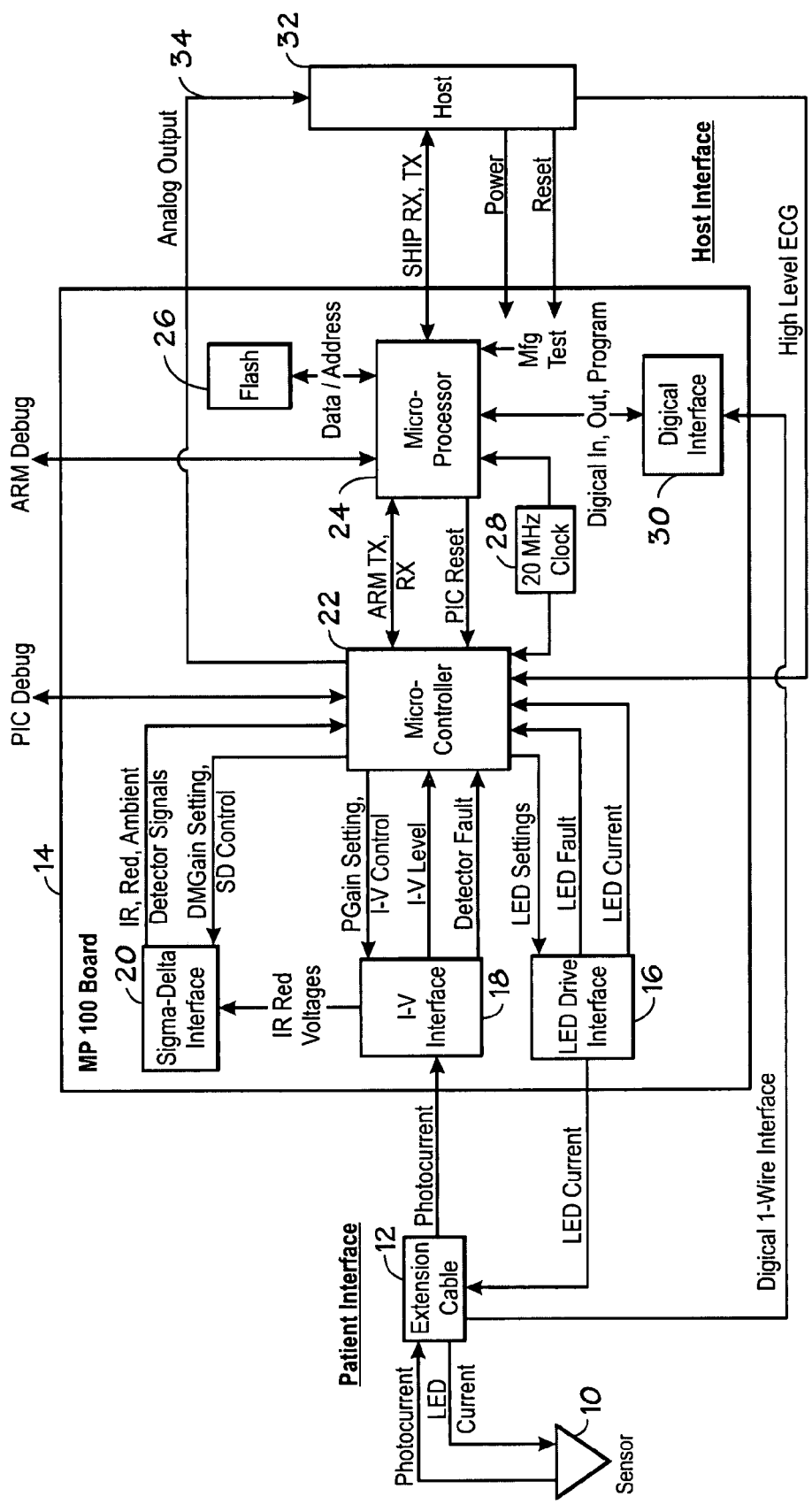
FIG. 1 is a block diagram of an oximeter incorporating the present invention.

FIG. 1 illustrates an embodiment of an oximetery system incorporating the present invention. A sensor 10 includes red and infrared LEDs and a photodetector. These are connected by a cable 12 to a board 14. LED drive current is provided by an LED drive interface 16 incorporating the present invention. The received photocurrent from the sensor is provided to an I-V interface 18. The IR and red voltages are then provided to a sigma-delta interface 20. The output of sigma-delta interface 20 is provided to a microcontroller 22 which includes a 10-bit A/D converter. Controller 22 includes flash memory for a program, and EEPROM memory for data. The processor also includes a controller chip 24 connected to a flash memory 26. Finally, a clock 28 is used and an interface 30 to a digital calibration in the sensor 10 is provided. A separate host 32 receives the processed information, as well as receiving an analog signal on a line 34 for providing an analog display.

LED Drive Circuit

FIG. 1 is a circuit diagram of the LED drive circuit 35 according to an embodiment of the invention, which forms a portion of LED drive interface 16 of FIG. 1. A voltage regulator 36 provides a voltage separate from the voltage supply for the overall oximeter circuitry. The output is provided as a 4.5 volt signal on line 38, with the level being set by the feedback resistor divider of resistors R89 and R90. The voltage on line 38 is provided to a FET transistor Q11 to an inductor L6. The current through inductor L6 is provided by a switch 40 to one of the capacitors C65 and C66, which store charge for the red and IR LEDs, respectively. A red/IR control signal on line 42 selects the switch position under control of the oximeter processor. A control signal LED PWM gate on line 44 controls the switching of transistor switch Q11.

Once the capacitors are charged up, the control signal on line 44 turns off switch Q11 and current is provided from either capacitor C65 or C66, through switch 40 and inductor L6 to either the red anode line 46 or the IR anode line 48 by way of transistors Q5 and Q6, respectively. A signal "red gate" turns on transistor Q5, while its inverse, "/red gate" turns off transistor Q7. This provides current through the red anode line 46 to the back to back LEDs 50, with the current returning through the IR anode to transistor Q8 and through resistor R10 to ground. Transistor Q8 is turned on by the signal "/IR gate" while the inverse of this signal, "IR gate" turns off transistor Q6. The signals are reversed when the IR anode is to be driven, with the "IR gate" and "red gate" signals, and their inverses, changing state, so that current is provided through transistor Q6 to IR anode 48 and returns through red anode 46 and through transistor Q7 to resistor R10 and ground. The "LED current sense" signal is read for calibration purposes not relevant to the present invention.

When the current from the capacitor C65 or C66 is provided through inductor L6 to the LEDs, and that current is switched off at the desired time, transistor Q11 is turned on so that the remaining current during the transition can be dumped into capacitor C64. This addresses the fact that the FET transistor switching is not instantaneous. Subsequently, C64 will dump its current through Q11 and inductor L6 into the capacitors when they are recharged.

Resistor R38 and capacitor C67 are connected in parallel to inductor L6 to protect against signal spikes, and provide a smooth transition. Connected to inductor L6 is a sampling circuit with a switch 52 controlled by an LED sample hold signal on line 54 to sample the signals and provide them through an amplifier 56 to a "LED current" signal on line 58 which is read by the processor. An integrating capacitor C68 is provided in parallel to amplifier 56. A switch 60 responds to a "clear LED sample" signal to operate the switch to short out the capacitor between samples.

The sample and hold circuit measures the voltage at node T18, between capacitor C69 and inductor L6, to determine the current. Capacitor C69 is 1/1000 of the value of capacitors C65 and C66. Thus, a proportional current is provided through C69, which is injected through switch 52 to integrating capacitor C68 to provide a voltage which can be measured at the output of amplifier 56 on line 58. The voltage measured by the processor on line 58 is used as a feedback, with the processor varying the width of the pulse delivered to transistor Q11 to selectively vary the amount of energy that's delivered to the capacitors 65 and 66, and then is eventually discharged to the LEDs 50. A PI (Proportional Integral) loop inside the processor then controls the PWM signal at Q11. This allows precise control of the LED intensity, allowing it to be maximized, if desired, without exceeding the desired limits (to avoid burning the patient, etc.).

The lower left of the diagram shows a "4.5 v LED disable" signal which is used by the microprocessor to turn off the voltage regulator 36 in certain instances. For example, diagnostics looking for shorts in a new sensor plugged in will turn off the voltage regulator if there is a problem with the LED line.

Zero Calibration Control

Figure 2:
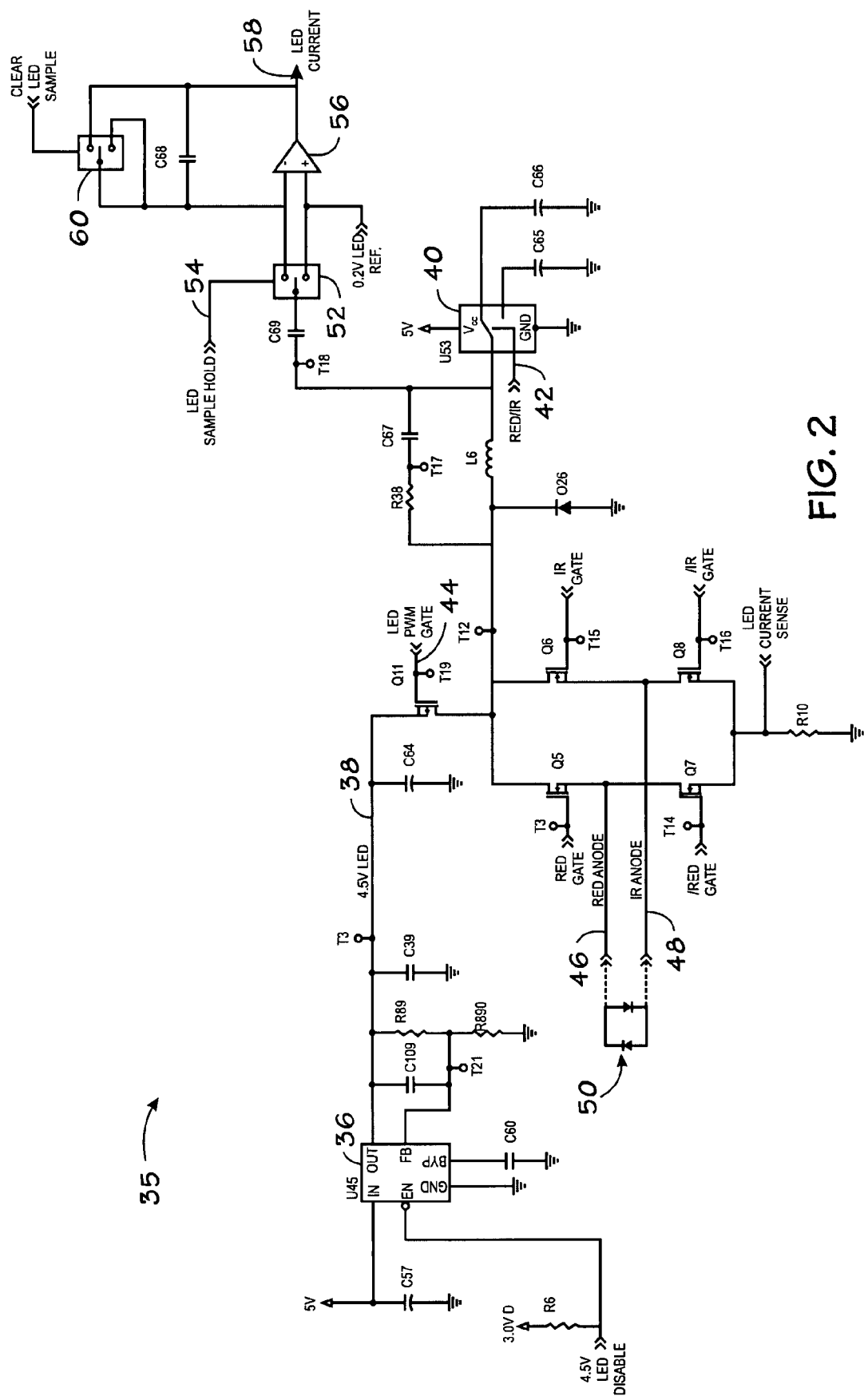
FIG. 2 is a circuit diagram of a LED drive circuit according to an embodiment of the present invention.
Figure 3:
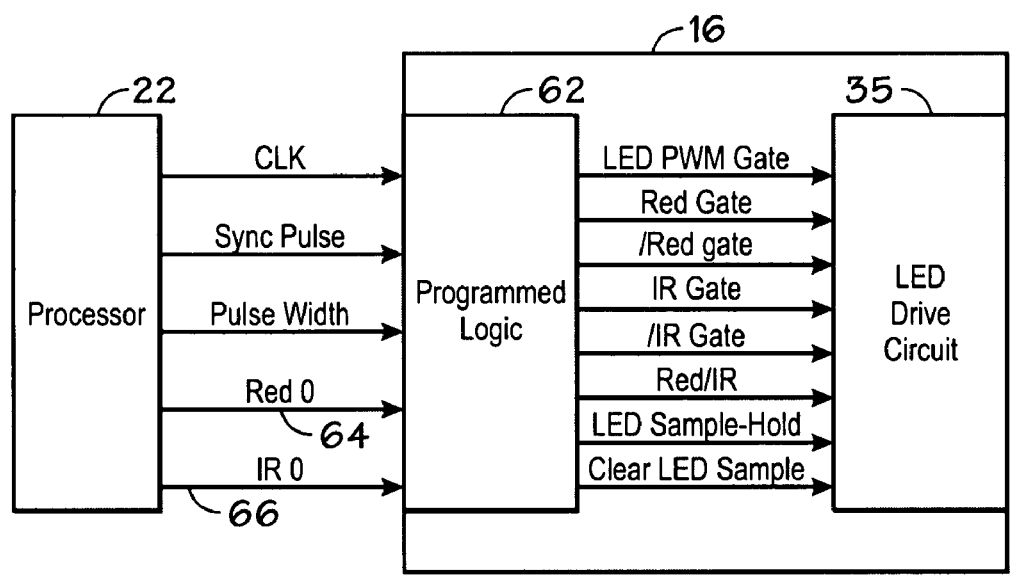
FIG. 3 is a block diagram of one embodiment of the logic for generating the timing and control signals for the circuit of FIG. 2.

FIG. 3 illustrates processor 22, from FIG. 1, connected to programmed logic 62, which is in the LED drive interface 16 in FIG. 1. Programmed logic 62 provides the different control signals used by the circuit of FIG. 2 in response to basic timing signals from the processor of a clock, a sync pulse, and a pulse width signal.

As can be seen, processor 22 also provides a red zero signal on a line 64 and an IR zero signal on a line 66. These two signals go to programmed logic circuit 62. Programmed logic circuit 62, in response to assertion of the red zero signal, will provide appropriate control signals on the red gate, /red gate, IR gate and /IR gate control outputs to control the drive transistors Q5, Q6, Q7, and Q8 of the LED drive circuit 35 of FIG. 2. In particular, assertion of the red zero signal will cause the red gate signal to turn off transistor Q5 and the /red gate signal to turn on the transistor Q7. The programmable logic for switching between the LEDs still functions, but is overridden by this zero signal. Thus, the red gate is held at its value regardless of efforts by the programmable logic state machine to cycle it on and off. Furthermore, because the /red gate signal turns on transistor Q7, the red anode line is tied to ground. Similarly, assertion of the IR zero signal on line 66 will cause program logic circuit 62 to turn off transistor Q6 with the IR gate signal, and turn on transistor Q8 with the /IR gate signal. Thus the IR anode line is tied to ground when the IR zero signal is asserted by the processor 22.

These control signals thus assure that current only flows through the red LED or the IR LED, without any leakage due to switching between them while the appropriate red zero or IR zero signal is asserted. This significantly reduces any switching leakage due to use of the duty cycle controls and any capacitively coupled switching transients.

As will be understood by those of skill in the art, the present invention can be embodied in other specific forms without departing from the essential characteristics thereof. For example, a different drive transistor structure could be used, such as for LEDs that are not configured back-to-back, but rather have separate connections which are separately driven. Accordingly, the foregoing description is intended to be illustrative, but not limiting, of the scope of the invention which is set forth in the following claims.

What is claimed is:

1. A pulse oximeter comprising:
a red drive line for a red light emitting diode (LED);
an infrared (IR) drive line for an IR LED;
a drive circuit coupled to the red and IR drive lines;
a processor configured to control the drive circuit, the processor having a red zero output line and an IR zero output line coupled to the drive circuit, wherein a control signal on zero output lines turns off a red or IR drive transistor providing forward current flow through the red and IR LEDs, respectively, and turns on a sink transistor coupling an anode of the red LED to ground or a sink transistor coupling an anode of the IR LED to ground; and
a logic circuit having inputs connected to the red and IR zero drive lines and outputs providing control signals to the drive circuit, wherein the logic circuit is programmed so that the red and IR zero drive lines override other control signals provided to the drive circuit.

2. The pulse oximeter of claim 1 wherein the LEDs are arranged back-to-back, such that the drive line for the red LED is the return line for the IR LED, and the drive line for the IR LED is the return line for the red LED.

3. A noninvasive device for determining physiological parameters comprising:
a monitor configured to be communicatively coupled to a sensor, the monitor comprising:
an LED drive interface configured to provide drive current to a plurality of LEDs of the sensor; and
a microcontroller coupled to the LED drive interface, wherein the microcontroller provides control signals to the LED drive interface, wherein the control signals activate transistors configured to couple an anode of at least one of the plurality of LEDs to grounds,
wherein the LED drive interface comprises a programmable logic device configured to provide control signals based on timing signals, the timing signals determining the timing of the drive current provided to the plurality of LEDs, wherein the programmable logic device is configured to receive zero signals from the microcontroller and override the timing signals in response to the zero signals.

4. The noninvasive device of claim 3 wherein the plurality of LEDs comprise a red LED and an infrared LED.

5. A method of operating a non-invasive medical device, the method comprising:

providing a first set of control signals to a drive current circuit, the drive current circuit providing current to a plurality of LEDs of the non-invasive medical device, the first set of control signals providing a timing scheme for operating the plurality of LEDs, the control signals being generated in response to a clock signal; and providing a second set of control signals to the drive current circuit, the second set of control signals being configured to couple an anode of at least one of the plurality of LEDs to ground, wherein providing the second set of control signals to the drive current circuit comprises providing a zero IR and a zero red signal to a programmable logic of the drive current circuit.

6. The method of claim 5, wherein providing the first set of control signals to the drive current circuit comprises providing a sync pulse and a pulse width signal to a programmable logic device of the drive current circuit.

7. The method of claim 5, wherein the second set of control signals is configured to turn off transistors through which the drive current is provided to the plurality of LEDs.

\* \* \* \* \*